US010258355B2

(12) United States Patent
Dhindsa

(10) Patent No.: US 10,258,355 B2
(45) Date of Patent: Apr. 16, 2019

(54) ENDOSCOPIC STONE-EXTRACTION DEVICE

(71) Applicant: INNON Holdings, LLC, Gilbert, AZ (US)

(72) Inventor: Avtar S. Dhindsa, Gilbert, AZ (US)

(73) Assignee: INNON Holdings, LLC, Gilbert, AZ (US)

( * ) Notice: Subject to any disclaimer, the term of this patent is extended or adjusted under 35 U.S.C. 154(b) by 260 days.

(21) Appl. No.: 15/175,893

(22) Filed: Jun. 7, 2016

(65) Prior Publication Data
US 2016/0278798 A1 Sep. 29, 2016

Related U.S. Application Data

(62) Division of application No. 14/452,179, filed on Aug. 5, 2014, now Pat. No. 9,655,634.
(Continued)

(51) Int. Cl.
*A61B 17/221* (2006.01)
*A61B 1/00* (2006.01)
(Continued)

(52) U.S. Cl.
CPC ........ *A61B 17/221* (2013.01); *A61B 1/00137* (2013.01); *A61B 1/018* (2013.01);
(Continued)

(58) Field of Classification Search
CPC .......... A61B 17/221; A61B 2017/2212; A61B 17/320016; A61B 17/32056; A61B 2017/0034; A61B 2017/00353; A61B 2017/00867; A61B 2017/2215; A61B 2017/2217
(Continued)

(56) References Cited

U.S. PATENT DOCUMENTS 3,955,578 A  5/1976 Chamness et al.
4,557,255 A  12/1985 Goodman
(Continued)

FOREIGN PATENT DOCUMENTS

JP   2004-16668   1/2004
WO   WO 1992/16153 A   10/1992

OTHER PUBLICATIONS

International Search Report and Written Opinion for PCT/US2014/037693 dated Oct. 8, 2014, 9 pages.
(Continued)

*Primary Examiner* — Katherine M Shi
(74) *Attorney, Agent, or Firm* — Spencer Fane LLP; Steven J. Laureanti

(57) ABSTRACT

An endoscopic stone-extraction device is provided comprising a support filament comprising an end portion, a sheath comprising a lumen, wherein the support filament is disposed in the lumen such that the sheath is slideable with respect to the support filament, and a handle comprising an actuator. Movement of the actuator in a first direction retracts the sheath and causes a shape to expand outside the lumen. Movement of the actuator in a second direction advances the sheath and causes the shape to at least partially collapse inside the lumen. Other embodiments are provided, and any of these embodiments can be used alone or in combination.

12 Claims, 14 Drawing Sheets

Related U.S. Application Data

(60) Provisional application No. 62/011,367, filed on Jun. 12, 2014.

(51) Int. Cl.
*A61B 1/018* (2006.01)
*A61B 1/307* (2006.01)

(52) U.S. Cl.
CPC ...... *A61B 1/307* (2013.01); *A61B 2017/2212* (2013.01); *A61B 2017/2215* (2013.01); *A61B 2017/2217* (2013.01)

(58) Field of Classification Search
USPC .............................. 606/113, 127, 128, 200
See application file for complete search history.

(56) References Cited

U.S. PATENT DOCUMENTS

| | | | |
|---|---|---|---|
| 4,590,938 A | 5/1986 | Segura et al. | |
| 4,612,931 A | 9/1986 | Dormia | |
| 4,873,978 A | 10/1989 | Ginsburg | |
| 4,927,426 A | 5/1990 | Dretler | |
| 5,066,295 A | 11/1991 | Kozak et al. | |
| 5,098,440 A | 3/1992 | Hillstead | |
| 5,190,542 A | 3/1993 | Nakao et al. | |
| 5,192,286 A | 3/1993 | Phan et al. | |
| 5,197,968 A | 3/1993 | Clement | |
| 5,201,740 A | 4/1993 | Nakao et al. | |
| 5,397,320 A | 3/1995 | Essig et al. | |
| 5,417,697 A | 5/1995 | Wilk et al. | |
| 5,423,805 A | 6/1995 | Brucker et al. | |
| 5,496,330 A | 3/1996 | Bates et al. | |
| 5,535,759 A | 7/1996 | Wilk | |
| 5,788,710 A | 8/1998 | Bates et al. | |
| 5,814,097 A | 9/1998 | Sterman et al. | |
| 5,910,154 A | 6/1999 | Tsugita et al. | |
| 5,911,734 A | 6/1999 | Tsugita et al. | |
| 5,957,932 A | 9/1999 | Bates et al. | |
| 5,989,266 A | 11/1999 | Foster | |
| 5,993,474 A | 11/1999 | Ouchi | |
| 6,007,546 A | 12/1999 | Snow et al. | |
| 6,010,512 A | 1/2000 | Chu et al. | |
| 6,015,415 A | 1/2000 | Avellent | |
| 6,027,520 A | 2/2000 | Tsugita et al. | |
| 6,042,598 A | 3/2000 | Tsugita et al. | |
| 6,059,796 A | 5/2000 | Bilitz et al. | |
| 6,077,274 A | 6/2000 | Ouchi | |
| 6,093,196 A | 7/2000 | Okada | |
| 6,096,053 A | 8/2000 | Bates | |
| 6,099,534 A | 8/2000 | Bates | |
| 6,165,179 A | 12/2000 | Cathcart et al. | |
| 6,165,200 A | 12/2000 | Tsugita et al. | |
| 6,168,603 B1 | 1/2001 | Leslie et al. | |
| 6,174,318 B1 | 1/2001 | Bates et al. | |
| 6,190,394 B1 | 2/2001 | Lind et al. | |
| 6,216,044 B1 | 4/2001 | Kordis | |
| 6,224,611 B1 | 5/2001 | Ouchi | |
| 6,235,026 B1 | 5/2001 | Smith | |
| 6,245,089 B1 | 6/2001 | Daniel et al. | |
| 6,270,513 B1 | 8/2001 | Tsugita et al. | |
| 6,280,451 B1 | 8/2001 | Bates et al. | |
| 6,346,116 B1 | 2/2002 | Brooks et al. | |
| 6,348,056 B1 | 2/2002 | Bates et al. | |
| 6,416,519 B1 | 7/2002 | VanDusseldorp | |
| 6,419,679 B1 | 7/2002 | Dhindsa | |
| 6,494,885 B1 | 12/2002 | Dhindsa | |
| 6,500,182 B2 | 12/2002 | Foster | |
| 6,537,297 B2 | 3/2003 | Tsugita et al. | |
| 6,551,327 B1 | 4/2003 | Dhindsa | |
| 6,652,537 B2 | 11/2003 | Mercereau et al. | |
| 6,673,080 B2 | 1/2004 | Reynolds et al. | |
| 6,679,893 B1 | 1/2004 | Iran | |
| 6,706,054 B2 | 3/2004 | Wessman et al. | |
| 6,743,237 B2 | 6/2004 | Dhindsa | |
| 6,752,811 B2 | 6/2004 | Chu et al. | |
| 6,786,865 B2 | 9/2004 | Dhindsa | |
| 7,041,116 B2 | 5/2006 | Goto et al. | |
| 7,087,062 B2 | 8/2006 | Dhindsa | |
| 7,169,154 B1 | 1/2007 | Que et al. | |
| 7,282,055 B2 | 10/2007 | Tsuruta | |
| 7,618,437 B2 | 11/2009 | Nakao | |
| 7,753,919 B2 | 7/2010 | Kanamaru | |
| 8,142,443 B2 | 3/2012 | Saleh | |
| 8,206,401 B2 | 6/2012 | Nakao | |
| 8,303,612 B2 | 11/2012 | Nakao et al. | |
| 8,308,739 B2 | 11/2012 | Wolfe | |
| 8,328,819 B2 | 12/2012 | Dilinger | |
| 8,328,820 B2 | 12/2012 | Diamant et al. | |
| 8,361,084 B2 | 1/2013 | Cheng et al. | |
| 8,469,970 B2 | 6/2013 | Diamant et al. | |
| 8,732,933 B2 | 5/2014 | Que et al. | |
| 8,828,022 B2 | 9/2014 | White et al. | |
| 8,852,204 B2 | 10/2014 | Gordon | |
| 8,974,469 B2 | 3/2015 | Taube et al. | |
| 8,998,946 B2 | 4/2015 | Morero | |
| 9,271,746 B2 | 3/2016 | Diamant et al. | |
| 2002/0169474 A1* | 11/2002 | Kusleika ................. | A61F 2/013 606/200 |
| 2004/0199048 A1 | 10/2004 | Clayman et al. | |
| 2004/0199201 A1* | 10/2004 | Kellett ................. | A61B 17/221 606/200 |
| 2006/0052798 A1 | 3/2006 | Kanamaru | |
| 2006/0293697 A1 | 12/2006 | Nakao et al. | |
| 2008/0009884 A1 | 1/2008 | Kennedy | |
| 2011/0106077 A1 | 5/2011 | Yanuma et al. | |
| 2012/0029556 A1 | 2/2012 | Masters | |
| 2014/0074147 A1* | 3/2014 | De Marchena ......... | A61F 2/013 606/200 |
| 2014/0364868 A1 | 12/2014 | Dhindsa | |

OTHER PUBLICATIONS

International Search Report dated Nov. 12, 2015 for PCT/US2015/032750.
Brochure, "Escape Nitinol Stone Retrieval Basket", Boston Scientific Corporation, 2009, 2 pages.
Brochure, Pietrow, MD, P., "Stone Cone TM Nitinol Retrieval Coil Technique", Boston Scientific Corporation, 2004, 4 pages.
Dialog Abstract, Binmoeller, K. et al., "Endoscopic Management of Bile Ducts", Journal of Clinical Gastroenterology, vol. 32, No. 2 pp. 106-118, Dialog File No. 144, Accession No. 14957807.
Dretler, Stephen P., "The Stone Cone: A New Generation of Basketry", The Journal of Urology, vol. 165, May 2001, pp. 1593-1596.
"OXO Good Grips Dough Blender with Blades" printed on Jul. 25, 2013 from http://www.amazon.com/OXO-Grips-Dough-Blender-Blades/dp/B000QJE480, pp. 1-6.
Picture, "omniFORCE TM Laser Stone Cage", printed on Jun. 10, 2013 from http://www.omnitechsystems.com/images/StoneCage.jpg, 1 pages.
NTrap Stone Entrapment and Extraction Device, printed on Jul. 25. 2013 from http://www.cookmedical.com/product/-/catalogidisplay?ds=uro_ntrap_webds, 1 page.

* cited by examiner

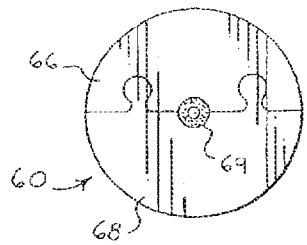
Fig. 3
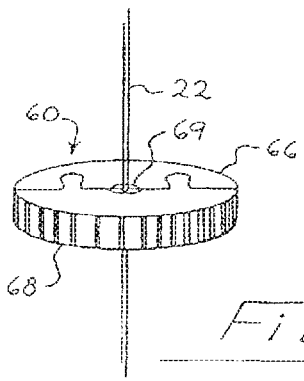
Fig. 5
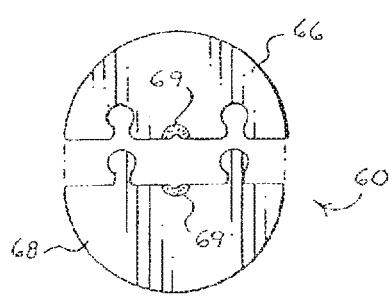
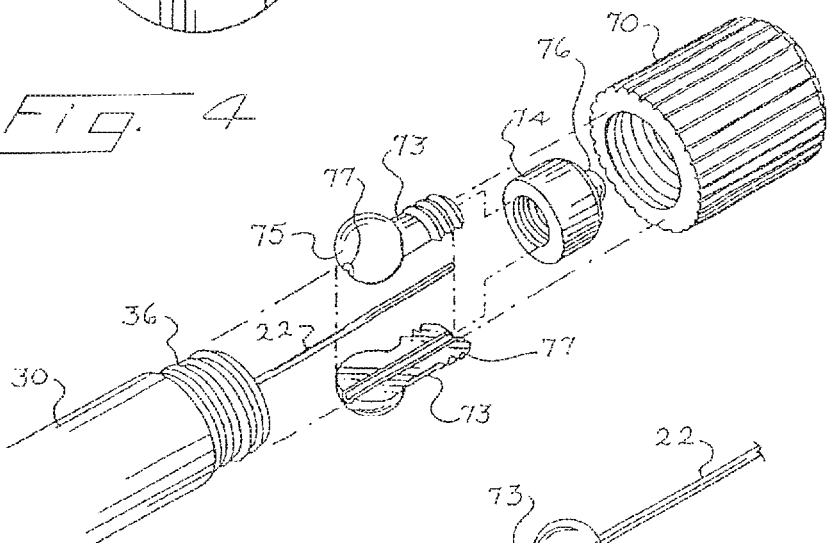
Fig. 4
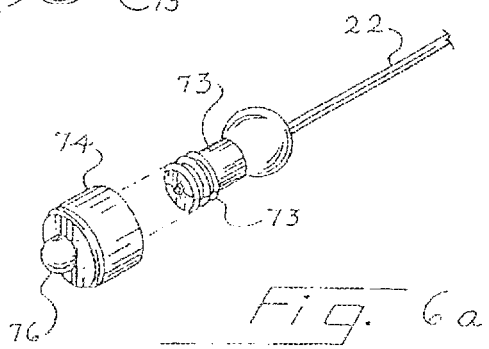
Fig. 6
Fig. 6a

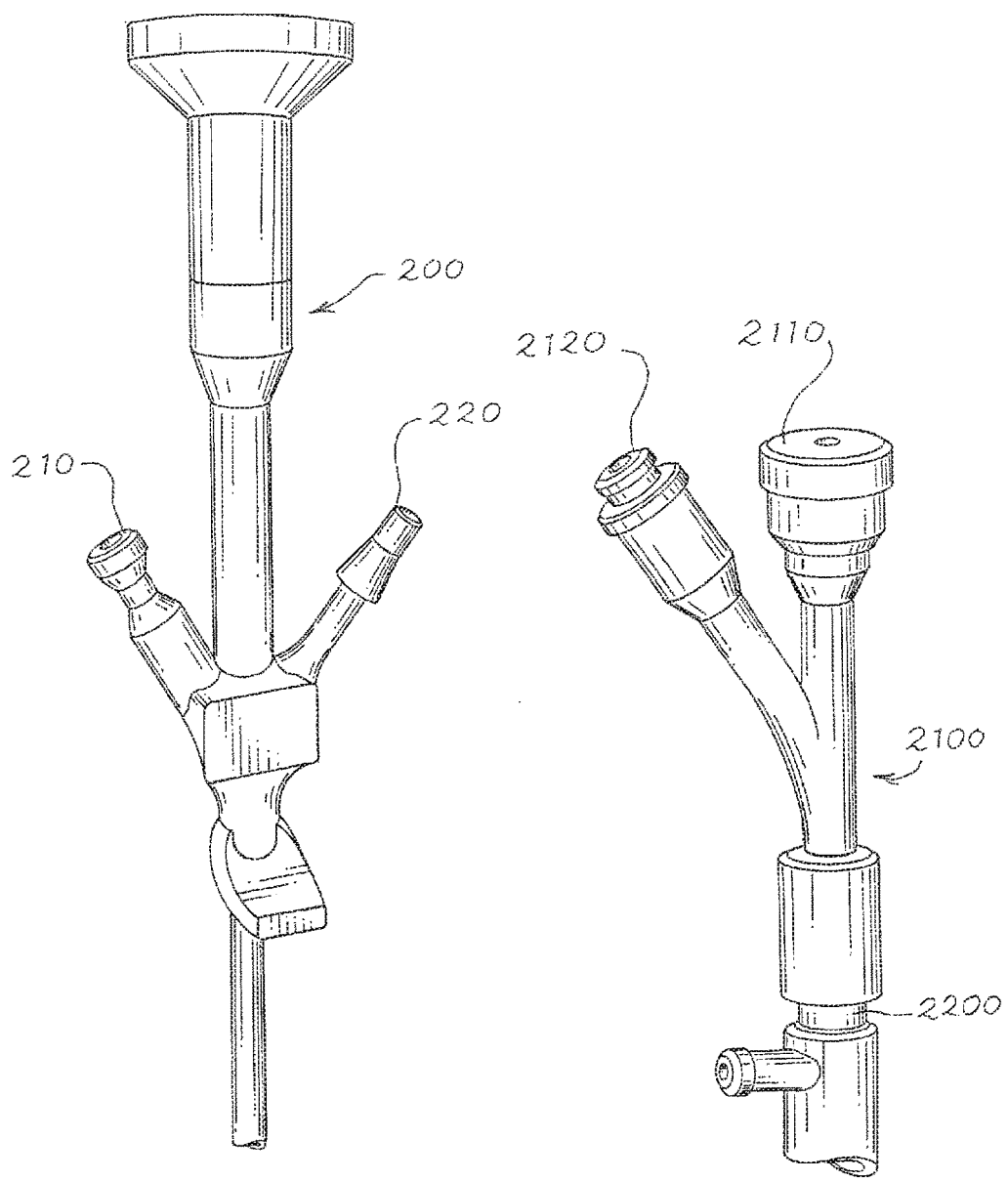

ENDOSCOPIC STONE-EXTRACTION DEVICE

CROSS-REFERENCE TO RELATED APPLICATIONS

This application is a divisional of U.S. patent application Ser. No. 14/452,179, filed on Aug. 5, 2014, entitled "Endoscopic Stone-Extraction Device," which claims the benefit under 35 U.S.C. § 119(e) to U.S. Provisional Application No. 62/011,367, filed Jun. 12, 2014, and entitled "Endoscopic Stone-Extraction Device." U.S. patent application Ser. No. 14/452,179 and U.S. Provisional Application No. 62/011,367 are assigned to the assignee of the present application. The subject matter disclosed in U.S. patent application Ser. No. 14/452,179 and U.S. Provisional Application No. 62/011,367 is hereby incorporated by reference into the present disclosure as if fully set forth herein.

BACKGROUND

Basket-type devices have been used for extracting stones such as ureteral stones, calaceal stones and other calculus and the like from the renal or biliary systems. Various types of stone extraction baskets have been used in the past to extract stones and stone fragments (or other debris) from various biological systems. A typical stone extraction basket includes a wire basket carried by one end of a wire that is received within the lumen of a sheath. The end of the wire opposite the basket is secured to a handle that is used to slide the sheath over the wire, thereby moving the basket into and out of the lumen of the sheath. When the basket is out of the sheath, it expands to receive a stone. The sheath is then moved toward the basket to reduce the size of the basket openings, and the basket and the enclosed stone are removed from the body. Ultrasonic, laser, and electro-hydraulic techniques have been used to fragment stones in situ. Typically, the stone fragments are left in the body to be excreted or can be attempted to be removed with a stone extraction basket or the like.

BRIEF DESCRIPTION OF THE DRAWINGS

FIGS. 3, 4 and 5 illustrate detailed views of a thumb wheel included in the embodiment of FIGS. 1 and 2.

FIG. 6 illustrates an exploded perspective view of a portion of the handle and the end portion of the wire of the embodiment of FIGS. 1 and 2.

FIG. 6A illustrates an exploded perspective view of the elements 73, 74 of FIG. 6 from another viewing angle.

FIG. 7 illustrates a cross-sectional view corresponding to that of FIG. 2 of another embodiment.

FIG. 8 illustrates a fragmentary side view of selected elements of the embodiment of FIG. 7.

FIG. 48 illustrates a two-port endoscope that can be used with an endoscopic stone-extraction device of an embodiment.

FIG. 49 illustrates a Y-adapter that can be used with the two-port endoscope of FIG. 48.

DETAILED DESCRIPTION

Introduction

Figure 1:
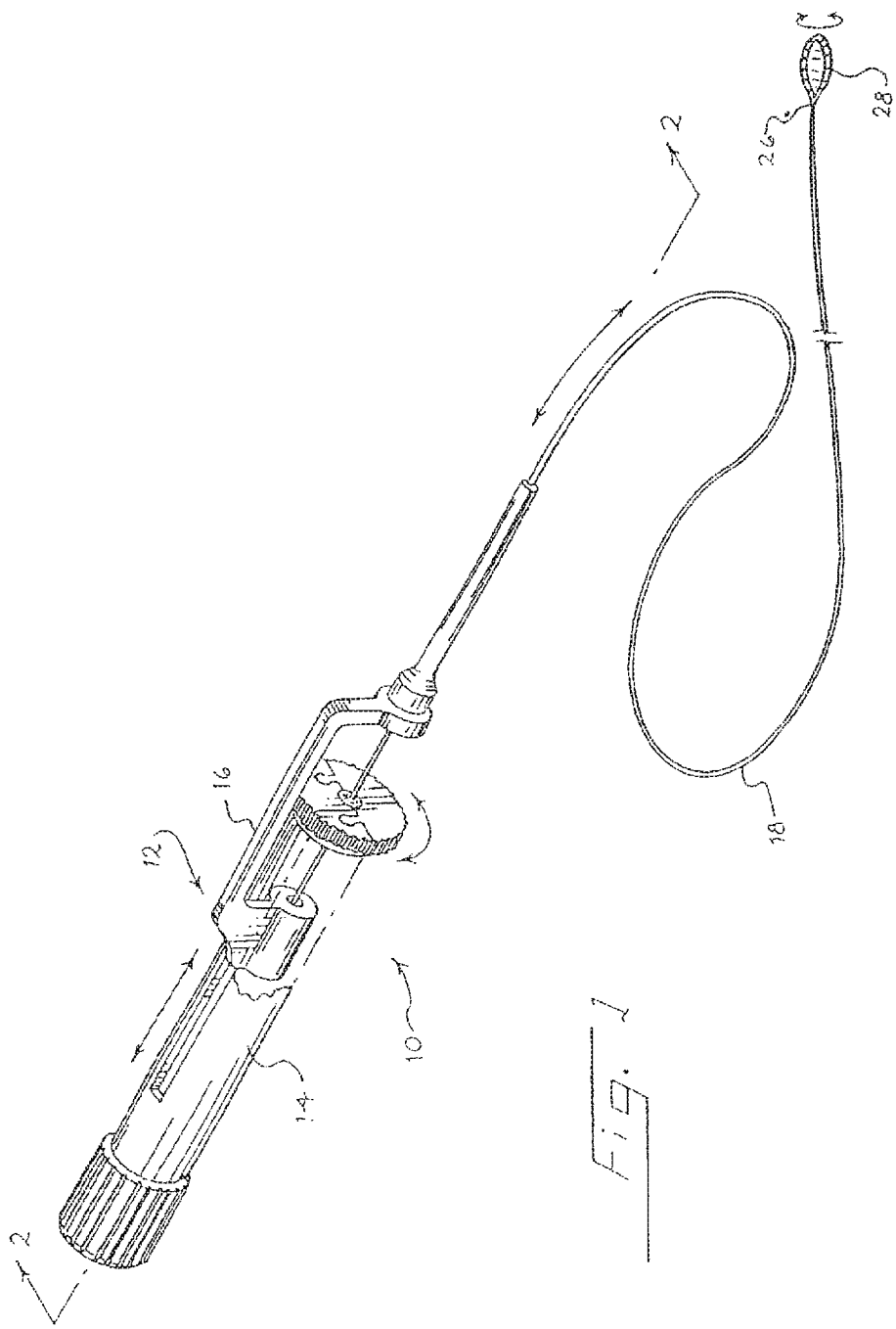
FIG. 1 illustrates perspective view of an endoscopic stone extraction device of an embodiment.

In a stone-removal procedure, an endoscope (e.g., a ureteroscope) is inserted into the body, with the distal end of the scope near the stone to be extracted. As shown in FIG. 48, an endoscope 200 typically has two ports 210, 220. One of the ports 210 is typically used as an irrigation port (for saline to be introduced into the extraction site), and the second port 220 is used for various instruments. In some situations, the second port 220 is initially used for the sheath that holds a stone extraction basket (however, other situations are possible, as will be discussed below).

The procedure begins with inserting the endoscope into the body (e.g., inserting the ureteroscope into the ureter) and identifying and locating the stone. Once the stone is identified, a decision is made whether the stone can be extracted out intact or whether the stone needs to be fragmented because it is too large to be extracted out. There are several technologies that are available for fragmentation, and a popular and effective technology is a laser. One of the problems faced during fragmentation is retropulsion, whereby the stone migrates up the ureter towards the kidney. Retropulsion makes the procedure more difficult and is associated with more complications.

To prevent migration of the stone, a mechanical device can be used as a backstop to the stone. When a mechanical backstop/trapping device is used, the scope is inserted, the stone is identified, and the mechanical backstop device is inserted through one of the ports of the scope (the other port is used as an irrigation channel). The mechanical backstop device is then placed beyond the stone and deployed. Since a two-port scope does not have any other access point for the laser fiber, the mechanical backstop is left in the body, while the uretroscope is removed from the body and then reinserted. The stone is identified again, and the laser fiber is then inserted into the open port to fragment the stone. The fragmented stone can be left inside the ureter to be passed out or can be dragged into the bladder and then extracted out either by irrigation or by using a stone basket (the mechanical backstop device usually is not very effective in removing stone fragments, which is why the separate stone basket is used).

Instead of using a mechanical backstop device, a gel can be inserted into the body just beyond the stone, and the patient's body temperature heats the gel to form a jelly that acts as a backstop to the stone. After the stone fragments have been removed, the physician introduces cold saline into the patient, which dissolves the jelly so it can drain out of the ureter. As another alternative to using a mechanical backstop device, a standard stone basket can be used to engage the stone. Once the stone is engaged, the basket filament and sheath are cut at the handle and left inside the body. The ureteroscope is then removed, and the procedure is carried out as mentioned above. However, some stone baskets, such as a four-wire basket, may not serve as an effective backstop since stone fragments can escape from the sides of the basket.

There are several difficulties associated with the current procedure. First, it is a multistep process, requirement the scope to be removed and re-inserted into the patient multiple times. Second, when a mechanical backstop device is used, it may not stay in place when the scope is removed and reinserted into the body (e.g., the backstop device can move up or down the ureter and sometimes into the kidney or come out in front of the stone instead of staying behind the stone). Third, stone fragments can escape around the backstop device (or a stone basket when a separate backstop device is not used) because these devices do not completely occlude the lumen.

The following endoscopic stone-extraction devices can function both as a trapping/backstop device and a stone extraction device, which eliminates at least one of the steps in the multi-step process described above. In addition to being more effective and useful, these devices can be easier to manufacture than traditional stone baskets.

Exemplary Endoscopic Stone-Extraction Devices

Figure 9:
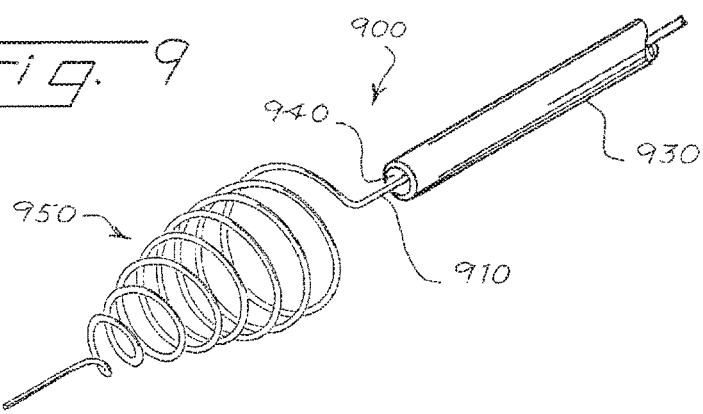
FIGS. 9-12 illustrate an endoscopic stone-extraction device of an embodiment having a tapered corkscrew shape.
Figure 10:
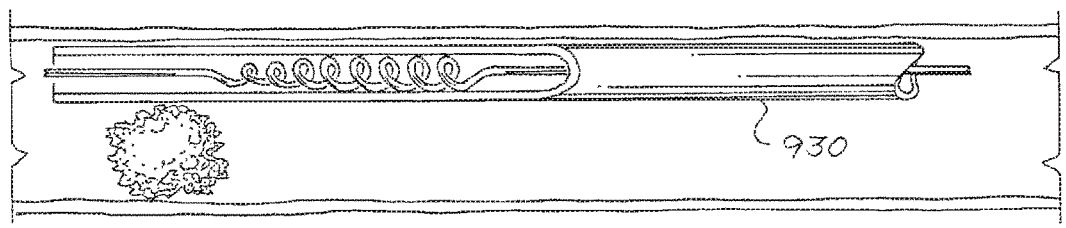
Figure 11:
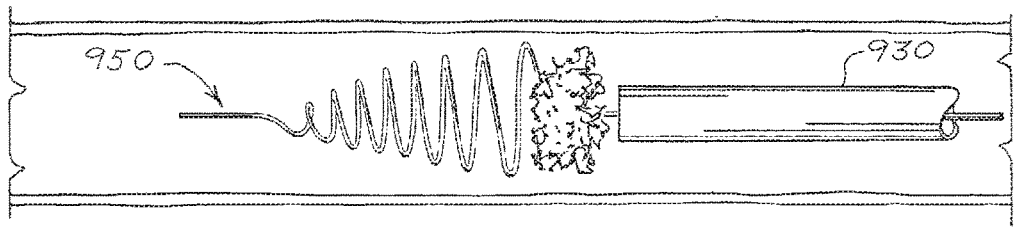
Figure 12:
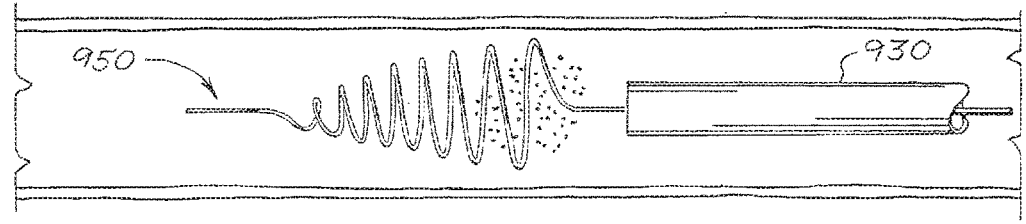
Figure 13:
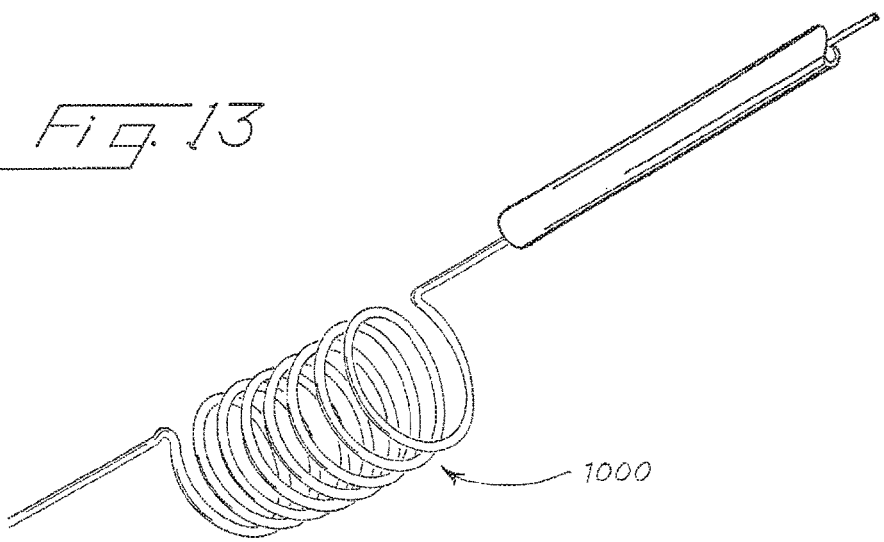
FIGS. 13-16 illustrate an endoscopic stone-extraction device of an embodiment having a non-tapered corkscrew shape.
Figure 14:
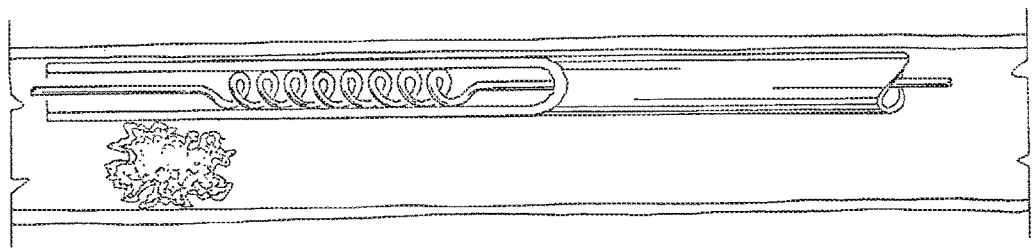
Figure 15:
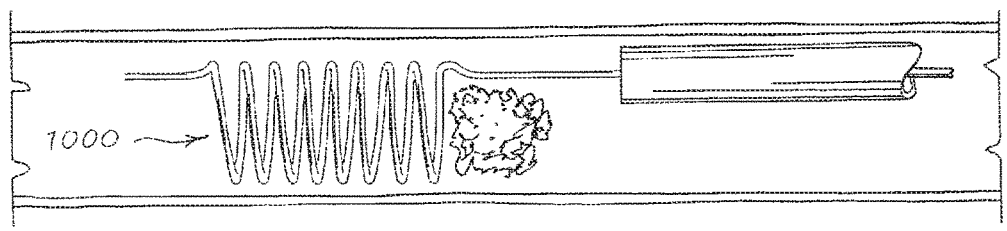
Figure 16:
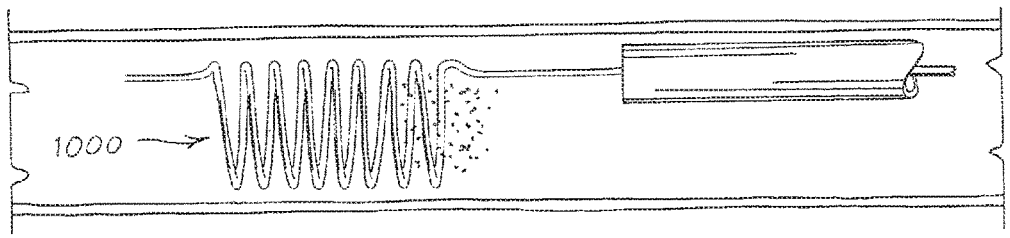
Figure 17:
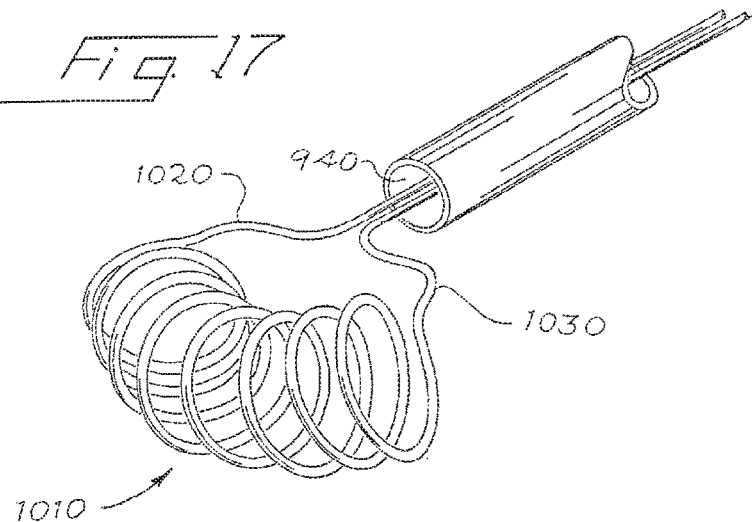
FIGS. 17-20 illustrate an endoscopic stone-extraction device of an embodiment having an arced corkscrew shape.
Figure 18:
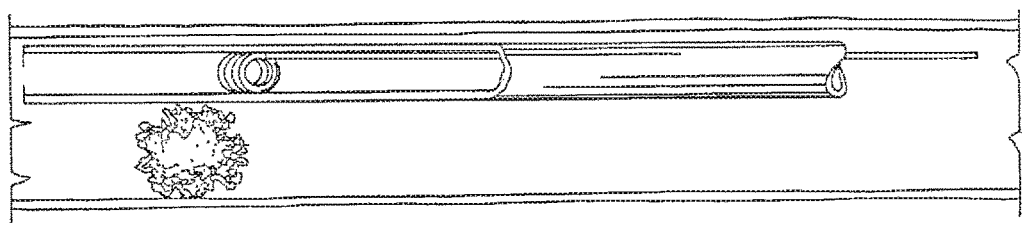
Figure 19:
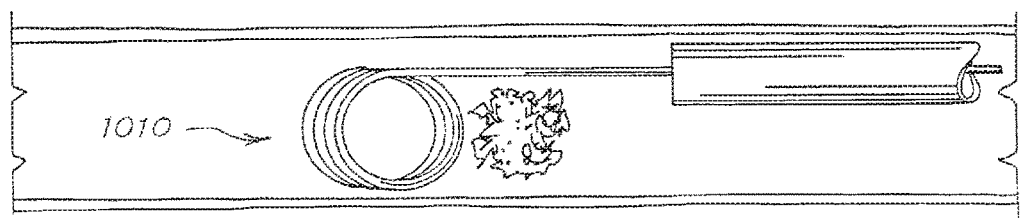
Figure 20:
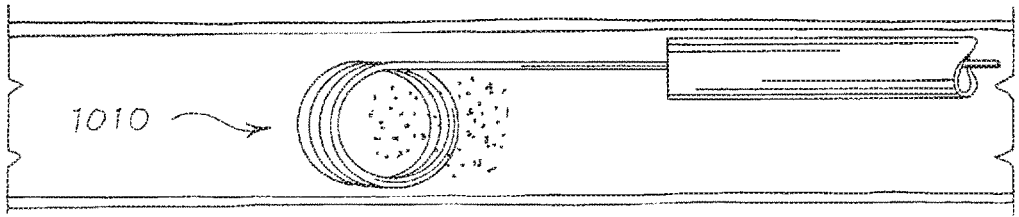
Figure 21:
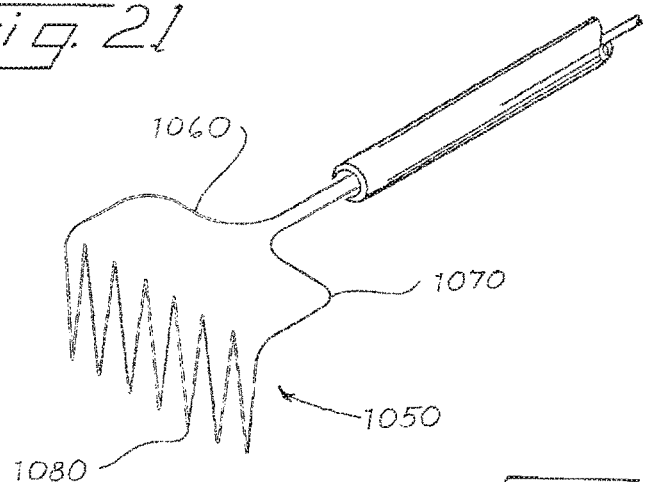
FIGS. 21-24 illustrate an endoscopic stone-extraction device of an embodiment having a rake shape.
Figure 22:
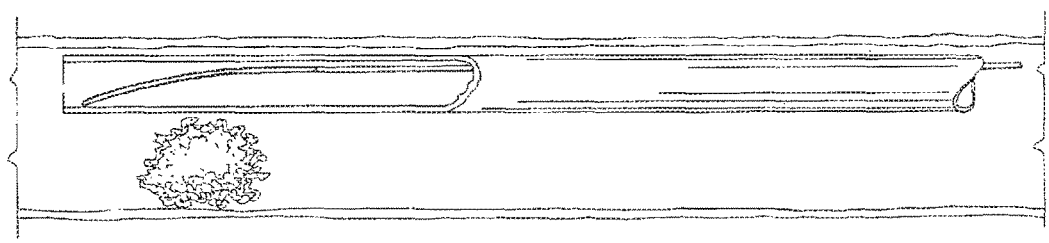
Figure 23:
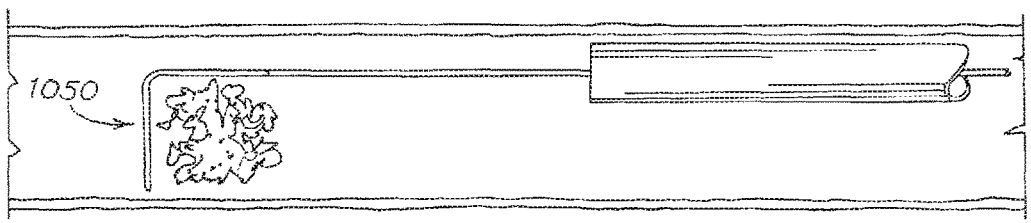
Figure 24:
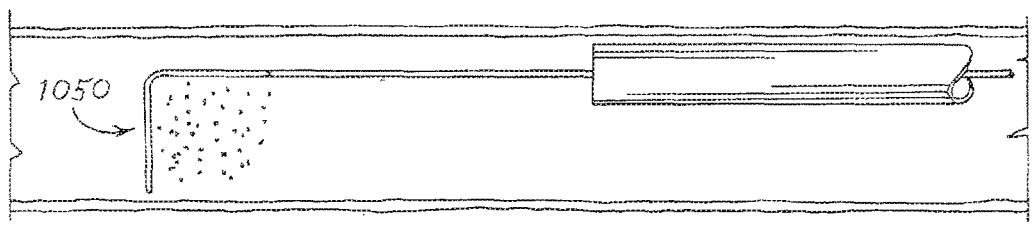
Figure 25:
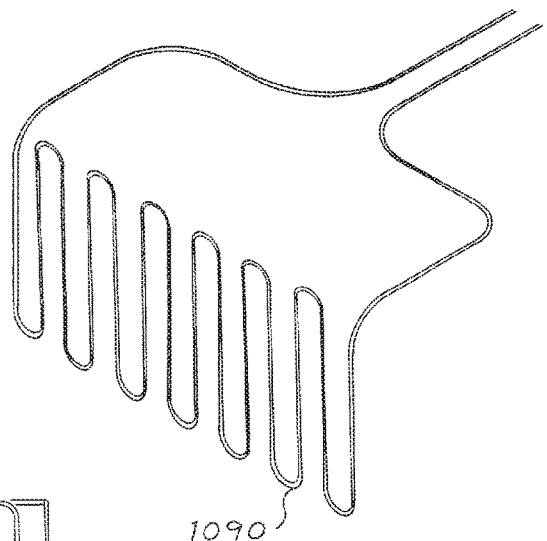
FIGS. 25-26 illustrate an alternate rake shape of an embodiment.
Figure 26:
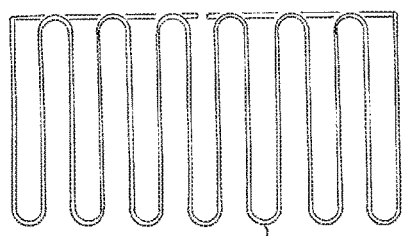
Figure 31:
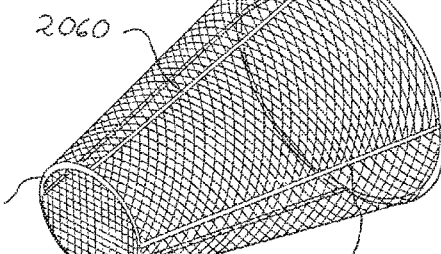
FIGS. 31-32 illustrate an endoscopic stone-extraction device of an embodiment having a meshed basket, circular shape.
Figure 32:
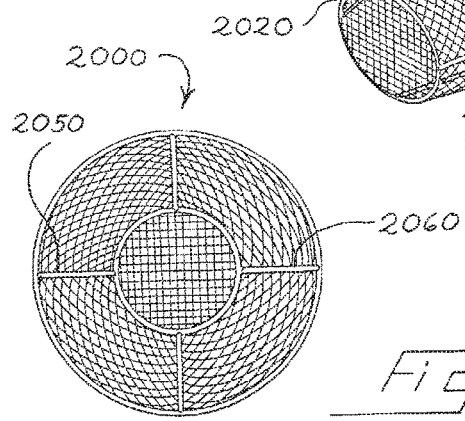
Figure 27A:
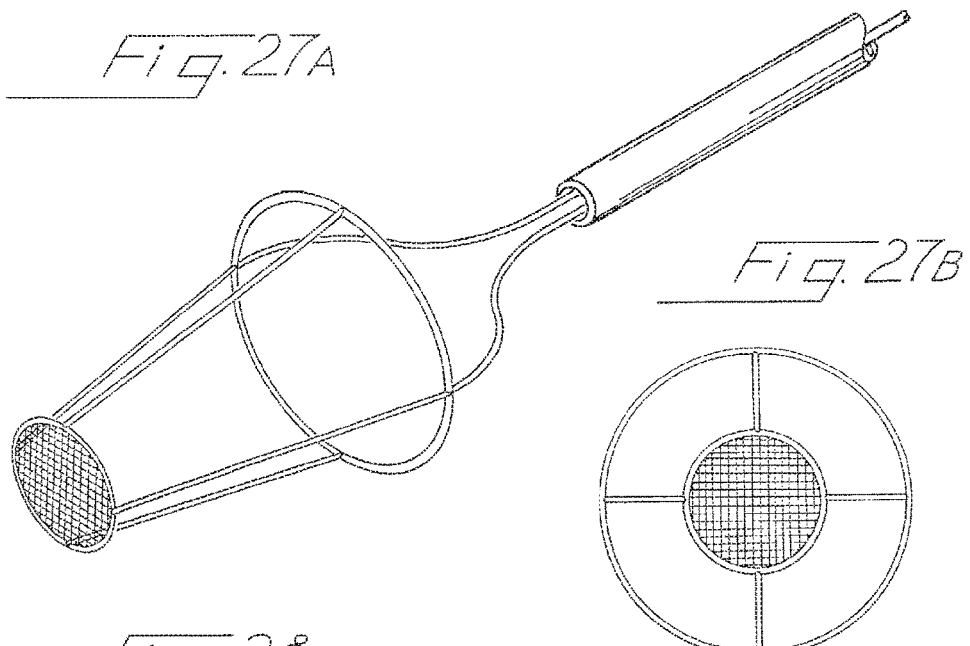
FIGS. 27A-30 illustrate an endoscopic stone-extraction device of an embodiment having an open basket, circular shape.
Figure 27B:
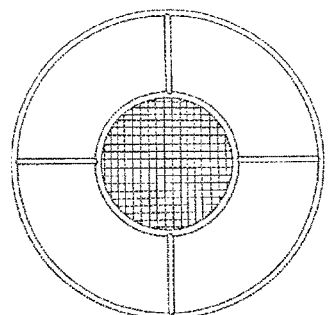
Figure 28:
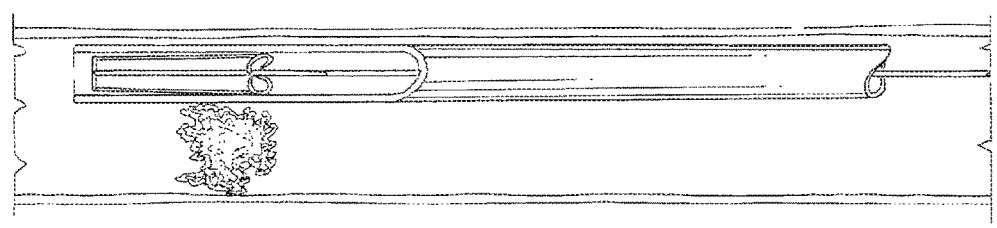
Figure 29:
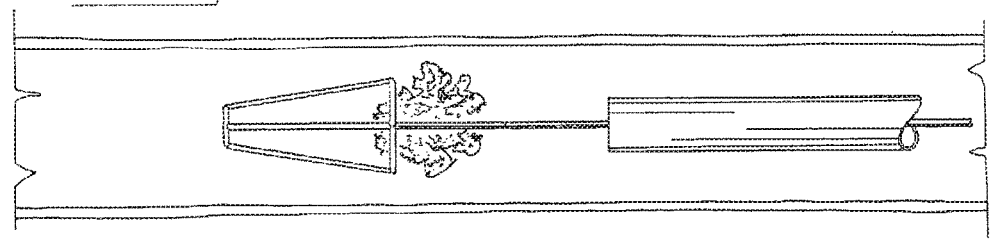
Figure 30:
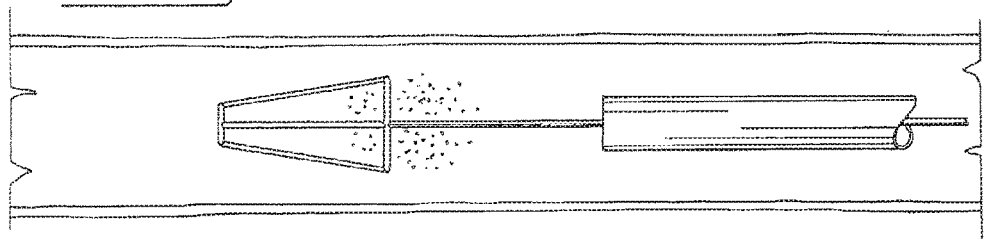
Figure 33:
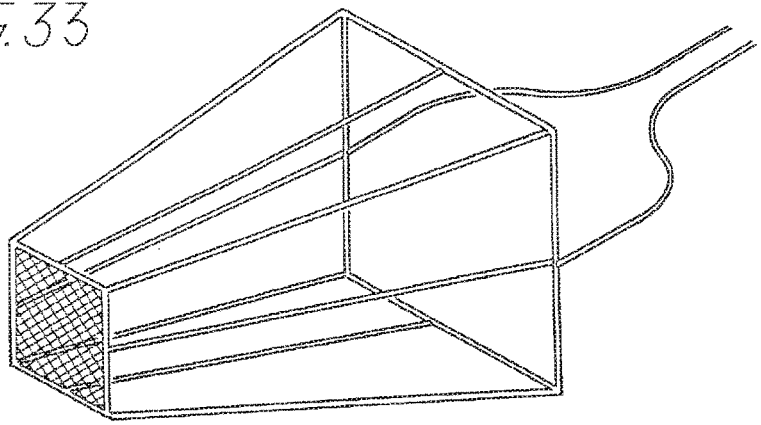
FIGS. 33-36 illustrate an endoscopic stone-extraction device of an embodiment having an open and closed basket, rectangular shapes.
Figure 34:
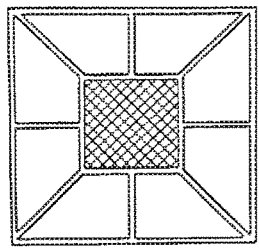
Figure 35:
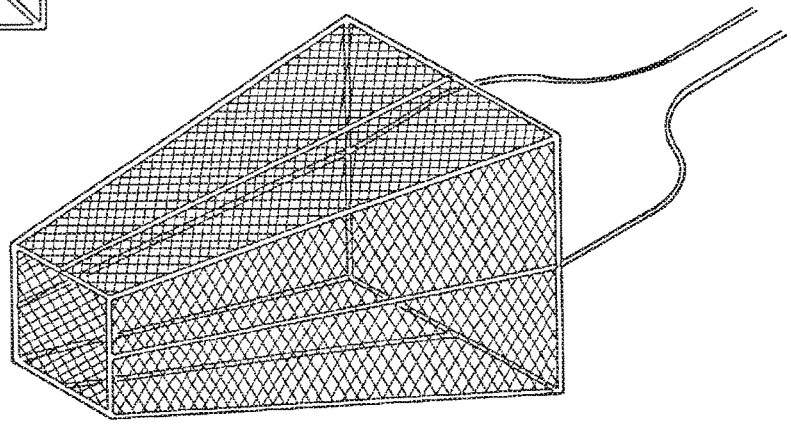
Figure 36:
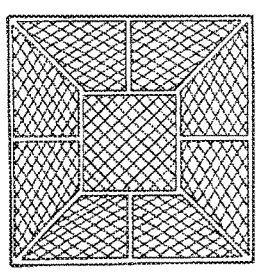
Figure 37:
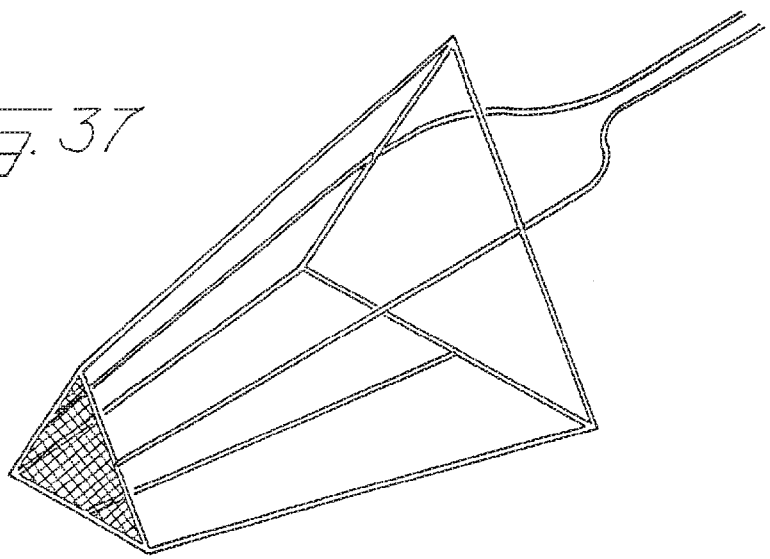
FIGS. 37-40 illustrate an endoscopic stone-extraction device of an embodiment having an open and closed basket, triangular shapes.
Figure 38:
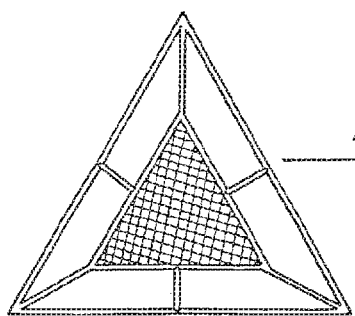
Figure 39:
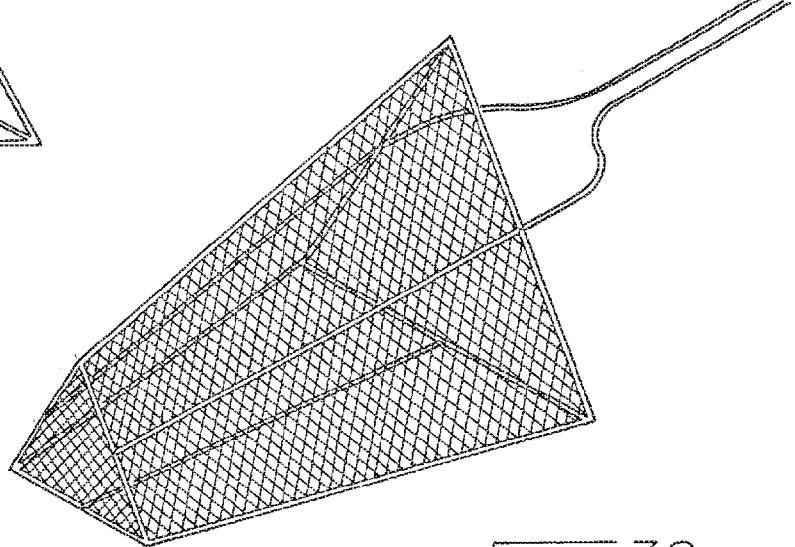
Figure 40:
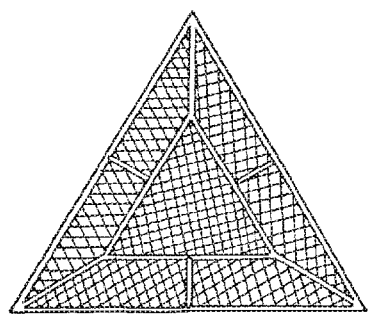
Figure 41:
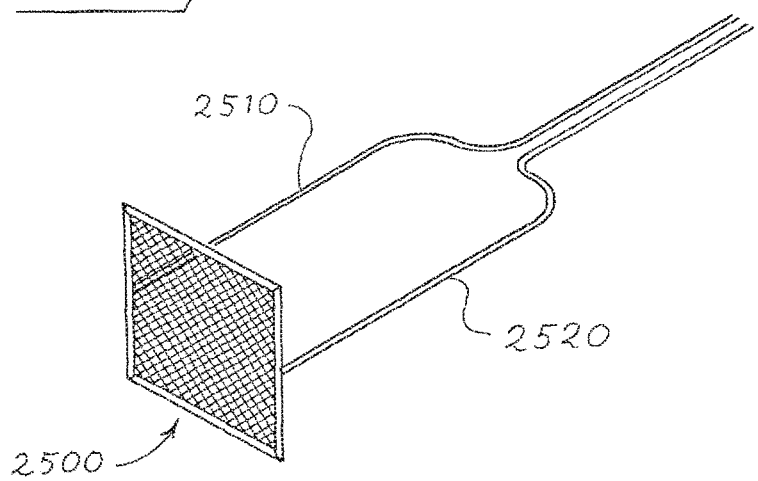
FIGS. 41-44 illustrate an endoscopic stone-extraction device of an embodiment having a two-dimensional meshed shape.
Figure 42:
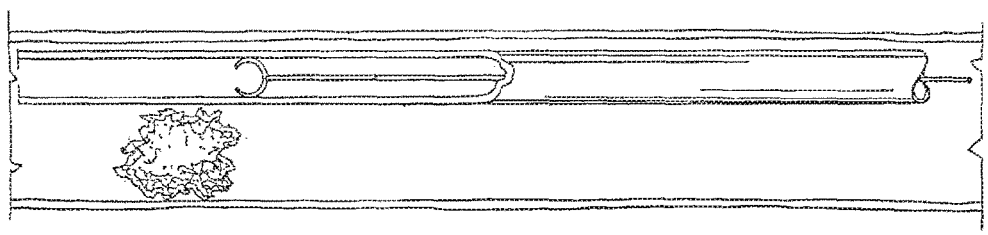
Figure 43:
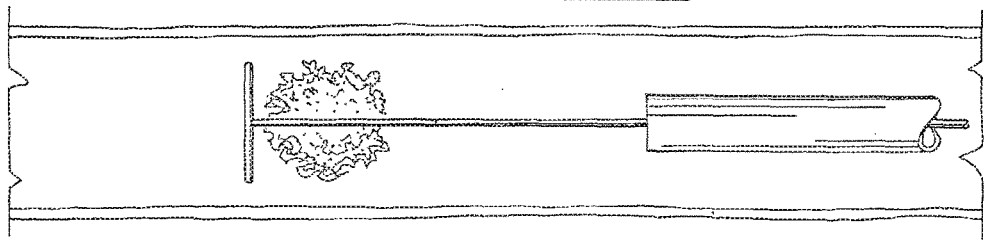
Figure 44:
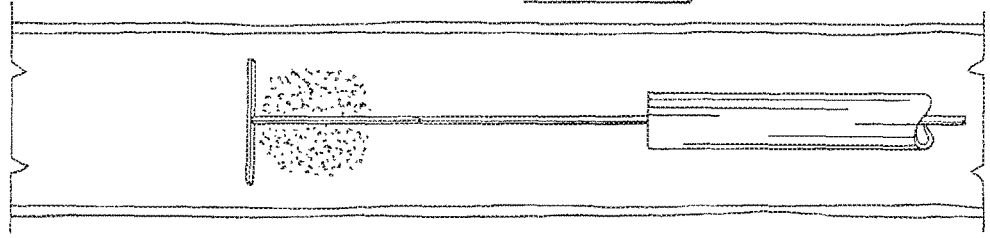
Figure 45:
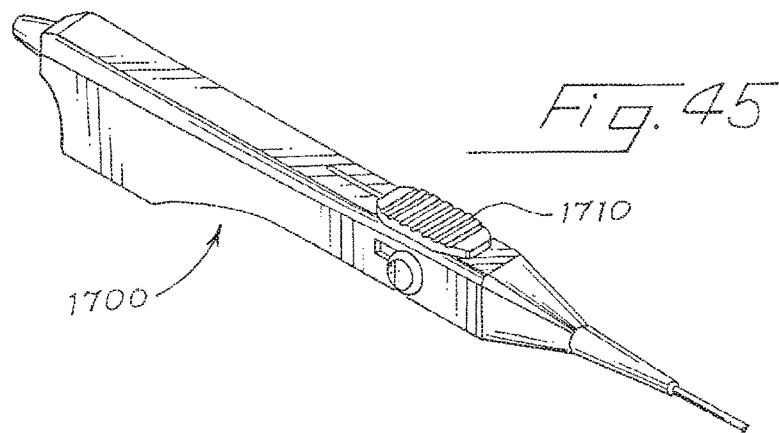
FIG. 45 illustrates a handle of an endoscopic stone-extraction device of an embodiment.

FIGS. 9-44 illustrate endoscopic stone-extraction devices of several embodiments. Turning first to FIG. 9, the endoscopic stone-extraction device 900 in this embodiment has a support filament 910 comprising an end portion and a sheath 930 comprising a lumen 940, wherein the support filament 910 is disposed in the lumen 940 such that the sheath 930 is slideable with respect to the support filament 910. A handle 1700 (see FIG. 45) comprises an actuator 1710. (Any type of handle with an actuator can be used, and other examples of handles are provided below. Details of any particular handle design (discussed herein or otherwise) should not be read into the claims unless explicitly recited therein). Movement of the actuator 1710 in a first direction retracts the sheath 930 and causes the end portion to expand outside the lumen in a corkscrew shape 950. Movement of the actuator in a second direction advances the sheath 930 and causes the corkscrew shape 950 to at least partially collapse inside the lumen 940. FIGS. 10-12 show how the endoscopic stone-extraction device can be deployed to hold a stone in place before destruction and collect the stone fragments after destruction.

In this embodiment, the corkscrew shape 950 is a conical-corkscrew shape that tapers from a larger portion closer to the lumen 940 to a smaller portion farther away from the lumen 940. However, other configurations are possible. For example, FIGS. 13-16 show a non-tapered corkscrew shape 1000, and FIGS. 17-20 show a corkscrew shape 1010 that is arced in a direction generally perpendicular to an axis of the lumen 940, wherein the corkscrew shape 1010 is connected to the support filament via a plurality of secondary filaments 1020, 1030.

In another embodiment (shown in FIGS. 21-24), movement of the actuator in a first direction retracts the sheath and causes the end portion to expand outside the lumen in a rake shape 1050, wherein the rake shape 1050 is connected to the support filament via a plurality of secondary filaments 1060, 1070. The rake shape can have pointed prongs 1080 (as in FIG. 21) or rounded prongs 1090 (as in FIGS. 25 and 26).

In yet another embodiment (shown in FIGS. 31 and 32), movement of the actuator in a first direction retracts the sheath and causes the end portion to expand outside the lumen in a basket shape 2000 that tapers from a larger portion 2010 closer to the lumen to a smaller portion 2020 farther away from the lumen, wherein the larger portion 2010 is an opening of the basket shape 2000, and the smaller portion 2020 is meshed. The basket shape 2000 is connected to the support filament via a plurality of secondary filaments 2030, 2040, and the larger and smaller portions 2010, 2020 are joined together by an additional plurality of filaments 2050, 2060. The sides of the basket shape can be meshed (as in FIGS. 31 and 32) or open (as in FIGS. 27A-30). Also, the smaller and larger portions can take any suitable shape, such as circular (as in FIGS. 27A-32), rectangular/square (as in FIGS. 33-36), or triangular (as in FIGS. 37-40). Of course, other shapes can be used.

In yet another embodiment, movement of the actuator in a first direction retracts the sheath and causes the end portion to expand outside the lumen in a two-dimensional mesh shape 2500 (see FIGS. 41-44) that is generally perpendicular to an axis of the lumen, wherein the two-dimensional mesh shape 2500 is connected to the support filament via a plurality of secondary filaments 2510, 2520. The two-dimensional mesh shape can take any suitable shape, such as a square (as in FIG. 41) or other shapes.

Regarding construction, the shapes can be formed from a plurality of individual filaments, all of which are joined (e.g., welded, soldered, swaged or otherwise held in place) to the support filament, or the shapes can be formed from a single filament. That single filament can be the support filament or can be a filament that is separate from but joined to the support filament. Further, shapes can be made from a shape memory metal, such as nitinol, although other materials can be used. In one embodiment, the shape can be made from preferably small, flexible, kink-resistant wires that are capable of collapsing together to fit within the lumen. Also, the shapes can be sized in any suitable fashion. For example, in one embodiment, the opening of the shape can be sized to admit a stone that is at least two millimeters in diameter (or less) or as large as 5 mm (or more) in diameter. Of course, other sizes and ranges can be used.

Exemplary Handles

Figure 46:
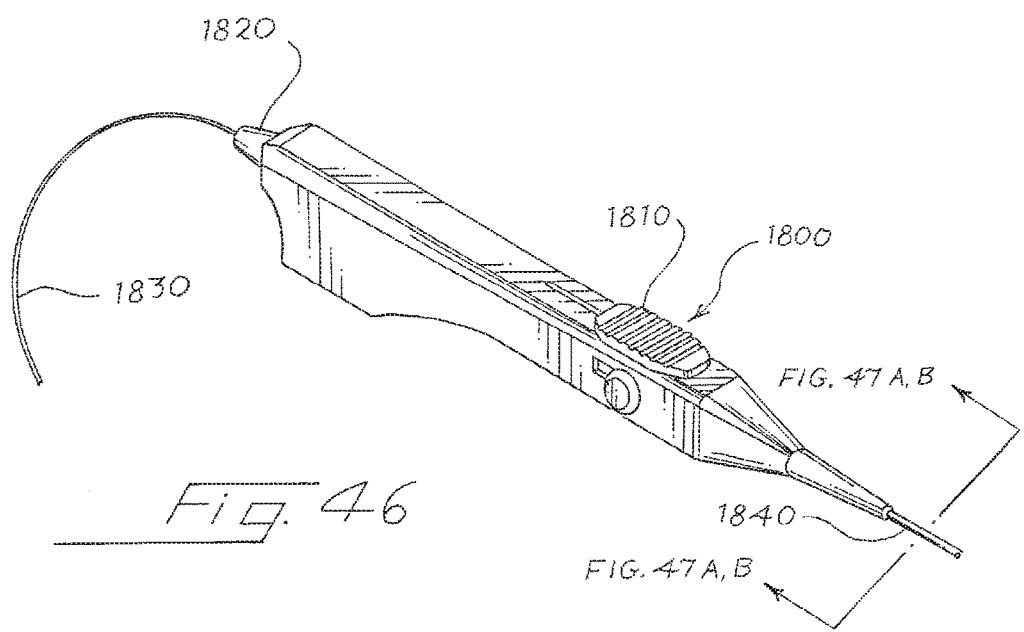
FIG. 46 illustrates a handle of an endoscopic stone-extraction device of an embodiment, wherein the handle has a laser fiber entry port.
Figure 47A:
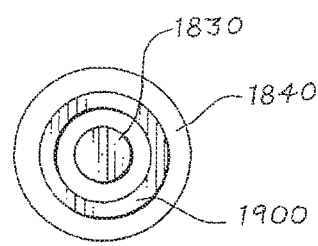
FIG. 47A illustrates a cross-section of a sheath of an embodiment where a laser fiber is internal to a stone-extraction filament.
Figure 47B:
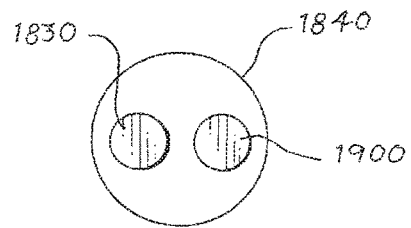
FIG. 47B illustrates a cross-section of a sheath of an embodiment where a laser fiber is external to a stone-extraction filament.

As noted above, any type of handle can be used with the stone-extraction devices of these embodiments. For example, the handle 1700 can simply be a device with an actuator 1710 to deploy the plurality of loops (as in FIG. 45). In another embodiment (see FIG. 46), the handle 1800 not only has an actuator 1810, but also has a port 1820 for a laser fiber 1830. (The omniFORCE™ Laser Stone Cage by Omnitech Systems is an example of such a handle.) As shown in FIGS. 47A and 47B, the laser fiber 1830 can either be internal to (FIG. 47A) or external to (FIG. 47B) the filament 1900, 1910 within the sheath 1840. The advantage of using this type of handle 1800 is that a two-port scope does not need to be removed and reinserted into the body in order to provide a free port for the laser fiber, as the laser fiber is already provided in the sheath 1840. Another way of obtaining this advantage of not removing the scope is by using a Y-adaptor 2100 (see FIG. 49) that would fit on one of the ports 220 of the scope 200, allowing both the stone-extraction sheath and the laser fiber to use the same port 220 on the scope 200. (The Y-adaptor used with the Escape® Basket from Boston Scientific is an exemplary adaptor.) In this alternative, it is preferred that the sheath and the laser fiber be sized so that they can both fit together inside the port 220.

As mentioned above, other handle designs can be used. The following paragraphs and drawings describe yet another handle design. Again, this and the other handle designs described herein are merely examples and should not be read into the claims.

Returning to the drawings, FIG. 1 shows an endoscopic stone extraction device 10 of an embodiment. The device 10 includes a handle 12 that in turn includes a grip 14 and a slide 16. As explained in greater detail below, the slide 16 is mounted to slide longitudinally along the length of the grip 14.

A tubular sheath 18 is secured to the slide 16. The sheath 18 defines a lumen 19, and the sheath 18 can be formed of any suitable flexible material. A strain relief collar 20 is provided at the point where the sheath 18 is secured to the slide 16 to reduce the incidence of kinking.

The device also includes a filament 22 having a first end 24 (FIG. 2) and a second end 26 (FIG. 1). The first end 24 is rotatably secured to the grip 14 (FIG. 2), and the second end 26 supports a stone extraction basket (this basket is of a different shape than the stone-extraction device discussed above, as this handle can be used with a variety of baskets). The filament 22 can be formed of any suitable material, and is typically formed of a flexible metallic wire. Preferably, the first end 24 is thicker and stiffer than the second end 26 to facilitate insertion and manipulation of the basket 28.

The following sections will first describe the handle 12 in greater detail.

Figure 2:
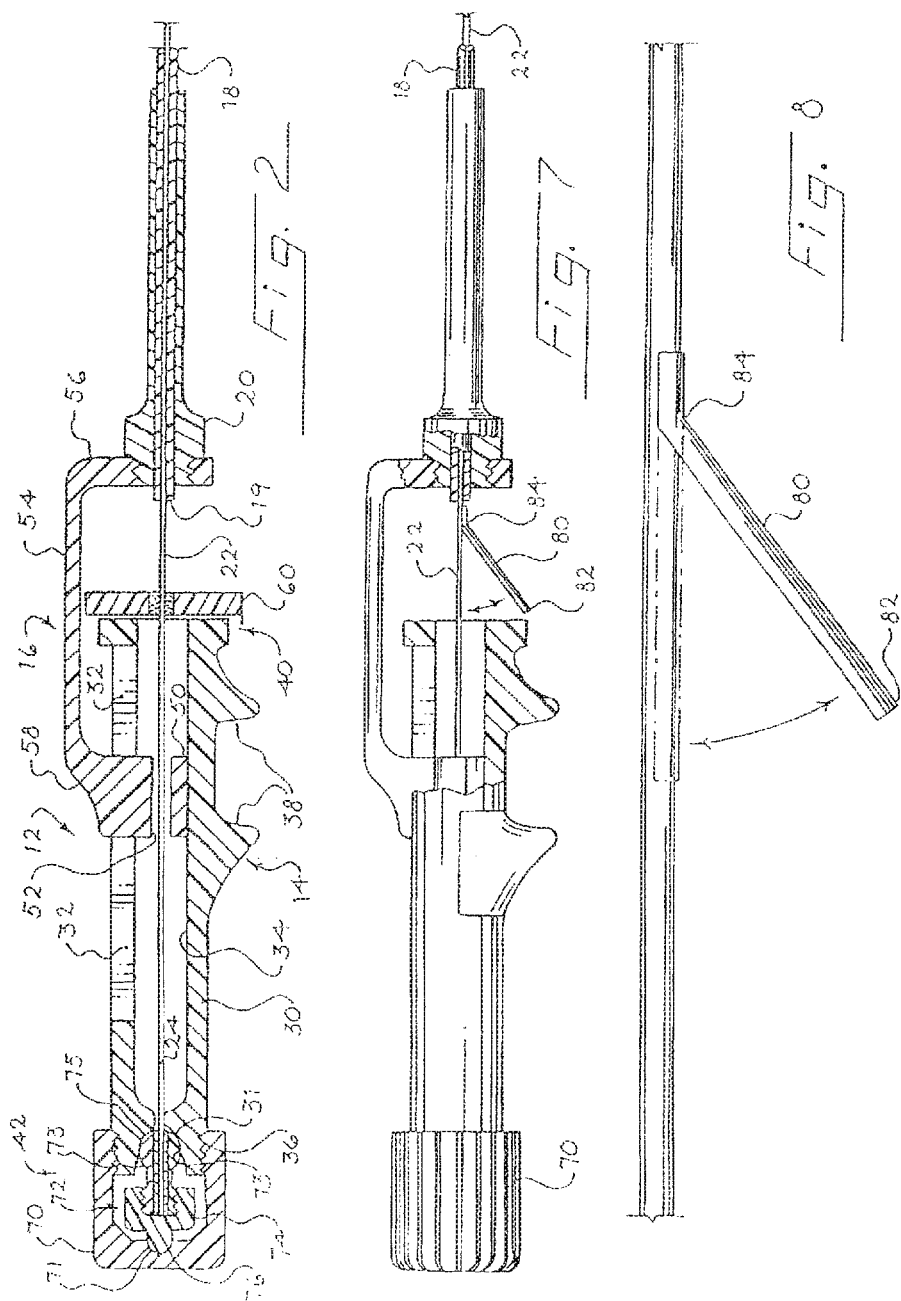
FIG. 2 illustrates a cross-sectional view taken along line 2-2 of FIG. 1.

As best shown in FIG. 2, the handle 12 includes a tube 30 that defines a longitudinally extending slot 32. The tube 30 forms a bore 34 and terminates at one end in external threads 36. Protruding elements 38 extend away from the perimeter of the tube 30 to facilitate the grasping of the tube 30 by a physician during use. For purposes of discussion, the portion of the tube 30 adjacent the external threads 36 will be referred to as the rear portion 42, and the opposite end of the tube 30 will be referred to as the front portion 40. The tube 30 may for example be formed of any suitable, moldable thermoplastic material, though the widest variety of materials can be adapted for use.

Continuing with FIG. 2, the slide 16 includes a guide cylinder 50 sized to slide along the bore 34 of the tube 30. This guide cylinder 50 defines a central opening 52 sized to pass the filament 22 with little or no friction therebetween. The slide 16 also includes an arm 54 that extends from the guide cylinder 50 through the slot 32 to a plate 56. The arm 54 holds the plate 56 in alignment with the centerline of the tube 30. The slide 16 includes a gripping portion 58 that can be pushed or pulled by a physician during use to move the slide 16 along the longitudinal axis of the tube 30. As before, a wide range of materials can be used for the slide 16, including any suitable thermoplastic material.

As shown in FIGS. 1-5, a disk 60 is provided. This disk 60 is positioned adjacent the front portion 40 of the tube 30. The disk 60 is clamped onto the filament 22, and the disk 60 is rotatable with respect to both the tube 30 and the slide 16. As shown in FIGS. 3-5, the disk 60 includes half-disks 66, 68 that snap together in a releasable manner. The half-disks 66, 68 carry respective elastomeric gripping portions 69 designed to grip the filament 22 therebetween when the half-disks 66, 67 are snapped together.

As best shown in FIGS. 1, 2, 6 and 6A, the handle 12 carries a threaded cap 70 that defines a set of internal threads sized to mate with the external threads 36. The cap 70 includes a socket 71 that bears on a chuck 72. When the cap 70 is tightened in place, the chuck 72 is held between the socket 71 and an internal socket 31 formed by the tube 30. The chuck 72 is free to rotate but not to translate with respect to the tube 30.

The chuck 72 includes two parts 73, each having a central groove 77 sized to clamp against the filament 22. The groove 77 may be lined with an elastomeric layer to ensure good frictional contact between the chuck 72 and the filament 22. Each part 73 defines external threads, and the parts 73 are clamped against the filament by a cap nut 74 such that the chuck 72 rotates and translates in unison with the filament 22. The chuck 72 forms a convex surface 75 that engages the socket 31, and a convex surface 76 that engages the socket 71. The surfaces 75, 76 are shaped to allow low-friction rotation of the chuck 72 and the filament 22 relative to the tube 30. Thus, the chuck 72 and associated elements carried by the tube 30 form a rotational joint. Other types of rotational joints may be used, including ball-and-socket joints. For example, a ball-and-socket joint may be included in the filament 22 near the first end 24, and the first end 24 may be fixed to the tube 30. Also, the filament may have an enlarged end that forms part of the rotational joint, and the enlarged end may be sized to fit through the lumen of the sheath 18. Alternatively, the enlarged end may be too large to fit through the lumen of the sheath, and may be removable from the body of the filament 22, e.g. by disassembling the enlarged end from the filament 22.

In use, the device 10 is assembled as shown in FIGS. 1 and 2. Initially, the slide 16 is advanced (i.e. moved to the right in the view of FIG. 2) to move the sheath 18 over the basket 28. This reduces the cross-sectional dimensions of the basket 28 and facilitates insertion of the basket 28 into a region of the body adjacent to the stone to be removed. The slide 16 is then moved to the left in the view of FIG. 2 to expose the basket 28, which resiliently assumes an enlarged operational shape.

It should be apparent from the foregoing discussion that rotation of the disk 60 and the filament 22 occurs without rotation of the sheath 18, the slide 16 or the handle 12. This arrangement facilitates rotation of the filament 22 and the basket 28 inside the lumen of the body cavity in which it is inserted, since friction between the sheath 18 and the endoscopic device and between the sheath 18 and adjacent tissue do not impede rotation of the filament 22 and the basket 28. Rotation of the filament 22 is guided by the rotational joint that includes the chuck 72. Once a stone has been captured within the basket, the slide 16 is then moved to the right in the view of FIG. 2 to move the sheath over at least a portion of the basket, thereby securely capturing the stone in the basket for removal.

On occasion, it may be necessary to remove the handle 12, the slide 16 and the sheath 18 while leaving the filament 22 and the basket 28 in place. This can readily be accomplished by unscrewing the cap 70 from the handle 12, removing the cap nut 74 from the parts 73, and then removing the parts 73, handle 12, slide 16 and sheath 18 from the filament 22.

The disk 60 is an example of a manipulator used to rotate the filament 22 relative to the handle 12. This manipulator can take other forms, including the form shown in FIGS. 7 and 8. The embodiment of FIGS. 7 and 8 is similar to that of FIGS. 1 and 2, except that the disk 60 has been replaced by a lever 80. This lever 80 defines a free end 82 and hinged end 84, and the free end 82 is positioned closer to the first end 24 of the filament 22 than is the hinged end 84. During normal use, the lever 80 is positioned as shown in FIG. 7 in an extended position. In this position the user can apply torques to the lever 80 and therefore to the filament 22 to rotate the filament 22 as described above. The hinged end 84 is connected to the filament 22 at a hinged joint (e.g. a living hinge or a multiple-part hinge) and the lever 80 can be moved to the retracted position shown in dotted lines in FIG. 8. In this retracted position, the lever 80 can be moved through the lumen of the sheath 18, thereby allowing the handle, slide and sheath to be removed from the filament 22 as described above.

CONCLUSION

It should be apparent from the foregoing detailed description that improved endoscopic stone extraction devices have been described that are well suited to the collection of a wide variety of stones, including stone fragments. The baskets described above are well suited for the removal of many types of debris, including for example, stones, stone fragments, and cholesterol plaque fragments. The devices described above can be used with the widest variety of endoscopes, including ureteroscopes, nephroscopes and other endoscopic devices, and they can be used within the lumens of many body tissues, including for example, ureters, bile ducts, and blood vessels.

As used herein, the term "stone" is intended broadly to encompass a wide variety of biological stones, calculus and the like, including fragments of stones, calculus and the like formed by any of the techniques described above or other techniques developed in the future. Urinary tract stones and biliary tract stones are two examples.

The term "end portion" is intended broadly to encompass the end of structure such as a filament along with an adjacent portion of the structure.

The term "surface" is intended broadly to encompass perforated surfaces. The term "filament" is intended broadly to encompass wires and other elongated structures formed of any of a wide range of materials, including metals, plastics, and other polymers.

Also, any of the embodiments in the following documents, which are hereby incorporated by reference, can be used in combination with the embodiments discussed herein: U.S. Pat. Nos. 6,743,237; 7,087,062; 6,419,679; 6,494,885; 6,551,327; and U.S. patent application Ser. No. 13/963,780.

The foregoing detailed description has discussed only a few of the many forms that this invention can take. For this reason, this detailed description is intended by way of illustration and not limitation. It is only the following claims, including all equivalents, that are intended to define the scope of this invention.

What is claimed is:

1. An endoscopic stone-extraction device comprising:
   a support filament comprising an end portion;
   a sheath comprising a lumen, wherein the support filament is disposed in the lumen such that the sheath is slideable with respect to the support filament; and
   a handle comprising an actuator;
   wherein movement of the actuator in a first direction retracts the sheath and causes the end portion to expand outside the lumen in a basket shape that tapers from a larger portion closer to the sheath to a smaller portion farther away from the sheath, wherein the larger portion is an opening of the basket shape and the opening is a first two-dimensional shape that is generally perpendicular to an axis of the lumen, wherein the smaller portion is meshed across a perimeter and the perimeter is a second two-dimensional shape that is smaller than the first two-dimensional shape and generally perpendicular to the axis of the lumen, and wherein the basket shape is connected to the support filament via two secondary filaments attached on opposite sides of the opening, and the larger portion and the smaller portion are joined together by at least two additional filaments; and
   wherein movement of the actuator in a second direction advances the sheath and causes the larger portion of the basket shape to at least partially collapse inside the lumen.

2. The endoscopic stone-extraction device of claim 1, wherein the first and second two-dimensional shapes are circular shapes.

3. The endoscopic stone-extraction device of claim 1, wherein the first and second two-dimensional shapes are rectangular shapes.

4. The endoscopic stone-extraction device of claim 1, wherein the first and second two-dimensional shapes are triangular shapes.

5. The endoscopic stone-extraction device of claim 1, wherein sides of the basket shape are meshed.

6. The endoscopic stone-extraction device of claim 1, wherein sides of the basket shape are open.

7. An endoscopic stone-extraction device comprising:
   a support filament comprising an end portion and configured to be disposed in a lumen of a sheath that is slideable with respect to the support filament; and
   the end portion configured, in response to retraction of the sheath, to expand in a basket shape that tapers from a larger portion to a smaller portion, wherein the larger portion is an opening of the basket shape, the smaller portion is a flat meshed surface coupled to the larger portion by at least two filaments, and the opening of the larger portion is substantially parallel to the flat meshed surface of the smaller portion.

8. The endoscopic stone-extraction device of claim 7, wherein the larger and smaller portions are circular shapes.

9. The endoscopic stone-extraction device of claim 7, wherein the larger and smaller portions are rectangular shapes.

10. The endoscopic stone-extraction device of claim 7, wherein the larger and smaller portions are triangular shapes.

11. The endoscopic stone-extraction device of claim 7, wherein sides of the basket shape are meshed.

12. The endoscopic stone-extraction device of claim 7, wherein sides of the basket shape are open.

* * * * *